United States Patent [19]

Levine

[11] 4,097,588
[45] Jun. 27, 1978

[54] MINERALIZING DENTAL MOUTHRINSE

[75] Inventor: Ronnie Stuart Levine, Leeds, England

[73] Assignee: National Research Development Corporation, London, England

[21] Appl. No.: 664,439

[22] Filed: Mar. 8, 1976

[30] Foreign Application Priority Data

Mar. 11, 1975 United Kingdom ............... 10044/75

[51] Int. Cl.² ............................................... A61K 7/18
[52] U.S. Cl. ......................................... 424/52; 424/57
[58] Field of Search .................................... 424/49–58

[56] References Cited

PUBLICATIONS

Levine, R. S. Archs Oral Biol. vol. 17, pp. 1005–1008 (1972).
Levine, R. S. et al. Archs Oral Biol. vol. 18, pp. 1351–1356 (1973).
Levine, R. S. British Dental Journal vol. 137, No. 4, pp. 132–134 (Aug. 20, 1974).

*Primary Examiner*—Shep K. Rose
*Attorney, Agent, or Firm*—Jacobs & Jacobs

[57] ABSTRACT

A dental mouthrinse is provided which is in the form of a clear solution saturated with respect to brushite and preferably also containing a source of fluoride ions such as to provide for example 3 to 20 ppm fluoride ions and a buffer with a molarity of for example 0.15 to 0.3M to provide a pH of 5.8 to 7.0. The mouth rinse is prepared by adding solid brushite to water to provide a solution containing excess solid brushite at a temperature of from 0° to 15° C, the solution is separated from excess brushite to provide a clear solution and the clear solution is allowed to come to an ambient temperature greater than 15° C. Further ingredients of the mouth rinse may be added together with the solid brushite or to the clear solution after it has been allowed to come to ambient temperature. The mouth rinse is capable of recalcifying both dentine and tooth enamel and is particularly suitable for recalcifying early decayed areas in teeth.

21 Claims, No Drawings

MINERALIZING DENTAL MOUTHRINSE

This invention relates to a mouth rinse or like composition. More particularly it relates to the preparation of a mouth rinse composition having recalcifying properties.

I have already described experiments which I have carried out to demonstrate the re-calcifying properties of dicalcium phosphate dihydrate (also known as "brushite" which designation is used hereinafter), in the presence of fluoride ions. Thus, in my first publication, (R. S. Levine, *Archs oral Biol.* Vol. 17, pp. 1005-1008, 1972, Pergamon Press) I described experiments with a remineralization system consisting of 0.5M phosphate buffer (pH 5.8 to 7.0) containing solid brushite to ensure saturation, and concentrations of sodium fluoride over the range of 0 to 100 ppm F. In two later publications (R. S. Levine et al, *Archs oral Biol.* Vol. 18, pp 1351-1356, 1973, Pergamon Press; R. S. Levine, *British Dental Journal,* Vol. 137, No. 4 pp 132-134, Aug. 20, 1974), I have described further experiments with this remineralization system.

In order to obtain as high a concentration as possible of dissolved calcium phosphate, brushite has been used instead of other calcium phosphate sources because of its somewhat higher solubility. However, brushite itself is not very soluble and in order to ensure saturation in the solution one has to work in practice with a solution containing some solid brushite.

Although on a small scale this may not appear disadvantageous it is a disadvantage on a large scale both from the point of view of manufacture and more so because the ultimate user has a mouth rinse with a solid deposit (excess brushite) which has to be shaken before use to disperse it, or from which the mouth rinse has to be carefully decanted.

It is an object of the present invention to provide a mouth rinse containing brushite which is a substantially clear solution whilst being saturated with brushite.

According to the present invention there is provided a method of making a mouth rinse containing brushite including the step of adding solid brushite to water to provide a solution containing excess solid brushite at a temperature of from 0° to 15° C, if desired in the presence of other ingredients of the mouth rinse, separating the clear solution from excess brushite, and allowing said solution to come to an ambient temperature greater than 15° C, if desired with addition of further ingredients of the mouth rinse.

Thus the brushite can be added to the water at a temperature in the range 0° to 15° C or the brushite can be added at a temperature outside this range and the solution and solid brushite subsequently brought to a temperatue in the range 0° to 15° C. The important feature is that whichever method is used a solution is produced which is saturated with respect to brushite at the selected temperature within the range 0° to 15° C.

By employing the method described above advantage is taken of a property of brushite, which I have noted, namely that its solubility coefficient is negative, that is to say it is more soluble at lower temperatures than at higher temperatures, in the range with which this invention is concerned. To illustrate this negative solubility coefficient brushite was continuously agitated with water at various temperatures for 5 hours and the calcium ion concentration in the solution was measured immediately by atomic absorption spectroscopy. The results were:

6° C—32 ppm
18° C—30.7 ppm
21° C—11.7 ppm.

The mouth rinse produced according to the invention is novel in the sense that a mouth rinse composition saturated with respect to brushite but also being in the form of a clear solution has not prevously been described.

According to the invention therefore there is further provided a mouth rinse composition saturated with respect to brushite and being in the form of a clear solution.

The mouth rinse according to the invention is capable of recalcifying both dentine and tooth enamel. Accordingly the mouth rinse may be used for treating or reducing the incidence of dental caries in humans by a method which simply comprises administering the mouth rinse composition so that it is in contact with the teeth for an adequate time. Use of the rinse for about 3 minutes 3 times daily is preferred but appreciable remineralization is to be expected from use for a lesser time daily. The mouth rinse is particularly suitable for the recalcification of early decayed areas in teeth.

The mouth rinse according to the invention generally contains in addition to brushite further components of which a buffer and a source of fluoride ions are the most important. Other components such as preserving agents, flavouring agents and antiseptic agents may be present.

As indicated above the solution of the brushite may be formed in the presence of some or all of the other ingredients of the mouth rinse. Thus all the components of the mouth rinse may be added to water at a temperature of 0° to 15° C and the mixture stirred for a time sufficient to ensure saturation with brushite.

In an alternative procedure one or more of the ingredients may be added later to the saturated solution of brushite.

In one embodiment of the invention the source of fluoride ions may be added by the user immediately before use and in that case the mouth rinse which is sold will not contain fluoride, this being added separately by the user according to the instructions with the mouth rinse. The term mouth rinse extends not only to a mouth rinse containing fluoride ions but also one without fluoride ions, these being added separately by the user.

The invention will now be described more fully with relation to the type of mouth rinse referred to in my publications mentioned above being one which contains brushite, a buffer and a source of fluoride ions.

An example of a mouth rinse of this type is as follows, the ingredients being sufficient for 10 litres of mouth rinse.

Potassium dihydrogen orthophosphate: 170 g
Disodium hydrogen orthophosphate dihydrate: 134 g
Dicalcium phosphate dihydrate (brushite): 10 g (an excess)
Sodium fluoride 0.001 % (5 ppm F): 0.10 g
Methyl-4hydroxybenzoate (preservative) 0.05 % 5.0 g
Water (distilled or deionised as required) to 10 litres.

The first two components of the composition constitute the buffer components. They make up a 0.2M buffer solution having a pH of about 6.5. The particular buffer components specified may be replaced by other potassium and sodium phosphate buffer salts or a combination of a phosphate and another salt e.g. sodium citrate may be used. A preferred buffer molarity is within the range of 0.15 to 0.3M. The pH is preferably witin the range of 5.8 to 7.0.

The sodium fuoride in the above composition may be replaced with other fluoride if desired, such as potassium fluoride. Preferably the amount of fluoride used is such that a concentration of fluoride ion of from 3 to 20 ppm is obtained in the final solution.

The preservative component is not essential but does prevent possible mould growth on storage. The preservative specified may be replaced by other accepted preservatives.

The above-described mouth rinse may be prepared by the method described below.

1. A mixing vessel of suitable volume made of polyethylene or other non-wetting material and fitted with a mechanical stirrer, a siphon tube for removal of the contents, an inlet tube for water and a suitable aperture for the addition of solids is provided. The siphon tube is connected via a valve to a storage reservoir of similar non-wetting material. The mixing vessel should either be housed in a cold room at from 1° to 15° C (preferentially 1° to 8° C) or may contain a cooling coil from a refrigeration plant to maintain this temperature.

2. The reagents in the proportions specified above are introduced into the mixing vessel. The contents are then mixed, preferably for a minimum of 3 hours, and then allowed to remain undisturbed, preferably for a minimum of 8 hours, to allow the excess brushite to settle.

3. The valve on the siphon tube is then opened and the supernatant solution transferred to the storage reservoir prior to dispensing into non-wetting containers. Step 2 is then repeated, making sure that excess brushite is present. A number of mixing vessels working continuously but out of phase and feeding a common reservoir can be used to maintain a continuous bottling process.

In a modification of the above method in order to produce a product having a particularly long shelf life it may be advantageous to omit the fluoride component from the above procedure and for the user to add it separately later.

In that case the fluoride may be supplied as a small volume of concentrated solution in a non-wetting ampoule for addition to the container of mouth rinse prior to dispensing or use. If the fluoride is omitted from the mixing stage described above the mixing and storage vessels may be made of normal wetting materials, e.g. glass rather than having to be of non-wetting material.

In use for addition to a 500 ml container of rinse to give 0.001 % NaF (5 ppm F) final concentration one may add 5 ml of a 0.1 % solution NaF or 1 ml of 0.5 % NaF, in a polyethylene ampoule.

I claim:

1. A mouthrinse composition saturated with respect to brushite, said composition being in the form of a clear solution and wherein said composition has been prepared by adding solid brushite to water to provide a solution containing excess solid brushite at a temperature of from 0° to 15° C., separating said solution from excess brushite to provide a clear solution, and allowing said clear solution to come to an ambient temperature greater than 15° C.

2. A composition according to claim 1 containing in addition a source of fluoride ions.

3. A composition according to claim 2 containing 3 to 20 ppm fluoride ions.

4. A composition according to claim 2 containing in addition a buffer.

5. A composition according to claim 4 in which said buffer has a molarity in the range 0.15 to 0.3M.

6. A composition according to claim 5 in which said buffe is potassium dihydrogen orthophosphate/disodium hydrogen orthophosphate dihydrate.

7. A composition according to claim 4 having a pH of 5.8 to 7.0.

8. A composition according to claim 1 containing at least one additional mouth rinse component selected from the group consisting of preserving agents, flavouring agents and antiseptic agents.

9. A method of making a mouth rinse in which solid brushite, a source of flouride ions and a buffer are added to water to provide a solution containing excess solid brushite at a temperature of from 0° to 15° C having a fluoride ion concentration of 3 to 20 ppm, a buffer molarity of 0.15 to 0.3M and a pH of 5.8 to 7.0 said solution is separated from excess brushite to provide a clear solution and said clear solution is allowed to come to an ambient temperature greater than 15° C.

10. A method of making a mouth rinse in which solid brushite is added to water to provide a solution containing excess solid brushite at a temperature of from 0° to 15° C, said solution is separated from excess brushite to provide a clear solution and said clear solution is allowed to come to an ambient temperature greater than 15° C.

11. A method according to claim 10 in which further ingredients of said mouth rinse are added to said water together with said solid brushite.

12. A method according to claim 10 in which further ingredients of said mouth rinse are added to said clear solution after it has been allowed to come to ambient temperature.

13. A method according to claim 10 in which said mouth rinse contans in addition a source of fluoride ions.

14. A method according to claim 13 in which said mouth rinse contains 3 to 20 ppm fluoride ions.

15. A method according to claim 13 in which said mouth rinse contains in addition a buffer.

16. A method according to claim 15 in which said buffer has a molarity in the range 0.15 to 0.3M.

17. A method according to claim 16 in which said buffer is potassium dihydrogen orthophosphate/disodium hydrogen orthophosphate dihydrate.

18. A method according to claim 15 in which said mouth rinse is produced with a pH of 5.8 to 7.0.

19. A method according to claim 15 in which said mouth rinse is produced containing at least one additional mouth rinse component selected from the group consisting of preserving agents, flavouring agents and antiseptic agents.

20. A method of treating or reducing the incidence of dental caries in humans which comprises administering a mouthrinse composition according to claim 1.

21. A method of treating or reducing the incidence of dental caries in humans which comprises administering a mouthrinse composition in the form of a clear solution saturated with respect to brushite, said solution having a pH of 5.8 to 7.0, containing 3 to 20 ppm fluoride ions and a buffer having a molarity in the range of 0.15 to 0.3M and wherein said composition has been prepared by adding solid brushite to water to provide a solution containing excess solid brushite at a temperature of from 0° to 15° C., separating said solution from excess brushite to provide a clear solution, and allowing said clear solution to come to an ambient temperature greater than 15° C.

* * * * *